US010220075B2

(12) United States Patent
Rosendahl et al.

(10) Patent No.: US 10,220,075 B2
(45) Date of Patent: Mar. 5, 2019

(54) AMINE PEGYLATION METHODS FOR THE PREPARATION OF SITE-SPECIFIC PROTEIN CONJUGATES

(71) Applicant: REZOLUTE, INC., Louisville, CO (US)

(72) Inventors: Mary S. Rosendahl, Broomfield, CO (US); Sankaram B. Mantripragada, Windsor, CO (US)

(73) Assignee: REZOLUTE, INC., Louisville, CO (US)

( * ) Notice: Subject to any disclaimer, the term of this patent is extended or adjusted under 35 U.S.C. 154(b) by 53 days.

(21) Appl. No.: 15/158,898

(22) Filed: May 19, 2016

(65) Prior Publication Data

US 2016/0354478 A1 Dec. 8, 2016

Related U.S. Application Data

(60) Provisional application No. 62/170,933, filed on Jun. 4, 2015.

(51) Int. Cl.
| | |
|---|---|
| A61K 47/60 | (2017.01) |
| A61K 38/26 | (2006.01) |
| A61K 38/28 | (2006.01) |
| A61K 38/29 | (2006.01) |
| A61K 9/50 | (2006.01) |
| A61K 38/27 | (2006.01) |

(52) U.S. Cl.
CPC ............ *A61K 38/26* (2013.01); *A61K 9/5031* (2013.01); *A61K 38/27* (2013.01); *A61K 38/28* (2013.01); *A61K 38/29* (2013.01); *A61K 47/60* (2017.08)

(58) Field of Classification Search
None
See application file for complete search history.

(56) References Cited

U.S. PATENT DOCUMENTS

| 5,359,030 A | 10/1994 | Ekwuribe |
| 5,438,040 A | 8/1995 | Ekwuribe |
| 6,191,105 B1 | 2/2001 | Ekwuribe et al. |
| 6,323,311 B1 | 11/2001 | Liu et al. |
| 6,362,254 B2 | 3/2002 | Harris et al. |
| 6,437,025 B1 | 8/2002 | Harris et al. |
| 6,541,543 B2 | 4/2003 | Harris et al. |
| 6,620,413 B1 | 9/2003 | DeSauvage et al. |
| 6,664,331 B2 | 12/2003 | Harris et al. |
| 6,774,180 B2 | 8/2004 | Kozlowski et al. |
| 7,053,150 B2 | 5/2006 | Kozlowski et al. |
| 7,223,803 B2 | 5/2007 | Harris et al. |
| 7,528,202 B2 | 5/2009 | Harris et al. |
| 7,557,183 B2 | 7/2009 | DiMarchi et al. |
| 7,714,088 B2 | 5/2010 | Harris et al. |
| 7,834,138 B2 | 11/2010 | Kozlowski et al. |
| 7,910,661 B2 | 3/2011 | Kozlowski et al. |
| 8,003,742 B2 | 8/2011 | Harris et al. |
| 8,084,572 B2 | 12/2011 | Kozlowski et al. |
| 8,183,340 B2 | 5/2012 | Glaesner et al. |
| 8,338,368 B2 | 12/2012 | DiMarchi et al. |
| 8,378,073 B2 | 2/2013 | Heywood |
| 8,383,380 B2 | 2/2013 | Kozlowski et al. |
| 8,617,531 B2 | 12/2013 | Cox et al. |
| 8,633,300 B2 | 1/2014 | Ostergaard et al. |
| 8,710,001 B2 | 4/2014 | Madsen et al. |
| 8,722,032 B2 | 5/2014 | Kozlowski et al. |
| 8,729,017 B2 | 5/2014 | DiMarchi et al. |
| 9,040,658 B2 | 5/2015 | Kozlowski et al. |
| 2005/0277586 A1 | 12/2005 | Taguchi et al. |
| 2006/0100144 A1 | 5/2006 | Lang et al. |
| 2007/0083006 A1 | 4/2007 | Hinds et al. |
| 2008/0026444 A1 | 1/2008 | Takakura et al. |
| 2009/0239790 A1 | 9/2009 | Pool et al. |
| 2010/0016550 A1 | 1/2010 | Dong et al. |
| 2012/0178914 A1 | 7/2012 | Henderson et al. |
| 2012/0329127 A1 | 12/2012 | Siekmann et al. |
| 2014/0128600 A1* | 5/2014 | Paul ..................... C07D 471/04 544/127 |

FOREIGN PATENT DOCUMENTS

| EP | 2877158 A2 | 6/2015 |
| KR | 20060029770 A | 4/2006 |

(Continued)

OTHER PUBLICATIONS

Ruhaak, et al., "2-Picoline-borane: A nontoxic reducing agent for Oligosaccharide labeling by reductive amination in Proteomics", 2010, vol. 10, pp. 2330-2336.

(Continued)

*Primary Examiner* — James W Rogers
(74) *Attorney, Agent, or Firm* — Kilpatrick Townsend & Stockton LLP

(57) ABSTRACT

Examples include a method of making a protein-PEG conjugate. The method may include providing an aqueous protein solution. The aqueous protein solution may include a protein, a pH buffer, and a chelating agent. The chelating agent may be chosen from the group consisting of an aminopolycarboxylic acid, a hydroxyaminocarboxylic acid, an N-substituted glycine, 2-(2-amino-2-oxoethyl) aminoethane sulfonic acid (BES), and deferoxamine (DEF). The method may also include introducing sodium cyanoborohydride and a methoxy polyethylene glycol aldehyde to the aqueous protein solution. The sodium cyanoborohydride in the methoxy polyethylene glycol aldehyde may have a molar ratio ranging from about 5:1 to about 1.5:1. The method may further include reacting the methoxy polyethylene glycol aldehyde with the protein to form the protein-PEG conjugate. The pH buffer may maintain a pH of the aqueous protein solution ranging from 4.0 to 4.4 during the reaction.

33 Claims, 16 Drawing Sheets

(56) References Cited

FOREIGN PATENT DOCUMENTS

| KR | 20120043205 A | 5/2012 |
|---|---|---|
| WO | 2004022004 A2 | 3/2004 |
| WO | 2009069983 A2 | 6/2009 |
| WO | 2011038900 A2 | 4/2011 |
| WO | 2011163473 A1 | 12/2011 |
| WO | 2012054861 A1 | 4/2012 |
| WO | 2012054882 A1 | 4/2012 |
| WO | 2012155780 A1 | 11/2012 |
| WO | 2015038938 A1 | 3/2015 |
| WO | 2015095406 A1 | 6/2015 |

OTHER PUBLICATIONS

Na, et al., "Capillary Electrophoretic characterization of PEGylated human parathyroid hormone with matrix-assisted laser desorption/ionization time-of-flight mass spectrometry in Analytical Biochemistry", 2004, vol. 331, pp. 322-328. Abstract.

\* cited by examiner

AMINE PEGYLATION METHODS FOR THE PREPARATION OF SITE-SPECIFIC PROTEIN CONJUGATES

CROSS-REFERENCE TO RELATED APPLICATION

This application is a nonprovisional of and claims priority to U.S. Provisional Patent Application Ser. No. 62/170,933, entitled "AMINE PEGYLATION METHODS FOR THE PREPARATION OF SITE-SPECIFIC PROTEIN CONJUGATES," Mary S. Rosendahl et al., filed on Jun. 4, 2015, which is related to U.S. Provisional Patent Application Ser. No. 62/086,294, entitled "PROTEINS AND PROTEIN CONJUGATES WITH INCREASED HYDROPHOBICITY," Mary S. Rosendahl et al., filed on Dec. 2, 2014, the entire disclosures of which are incorporated herein by reference, for all purposes, as if fully set forth herein.

BACKGROUND

Delivery of a drug, hormone, protein, or other medically active agent into a patient faces a number of challenges. The medically active agent has to be delivered into the patient. Two such ways are ingestion and injection. With ingestion the drug may have to pass through a patient's digestive system before reaching the bloodstream or targeted area for treatment. Injection may allow the medically active agent to reach the bloodstream or targeted area for treatment quickly or directly, but injection may be inconvenient or painful for the patient. Once in the body, the concentration of the medically active agent as a function of time may vary depending on the type of medically active agent, the attachment of different functional groups or molecules on the medically active agent, the encapsulation of the medically active agent, or other factors. If the concentration of the medically active agent decreases below a threshold, the medically active agent may need to be administered once again. Many medically active agents have to be administered frequently, including several times a day. A more frequent administration schedule may increase the inconvenience to the patient, may decrease the compliance rate by patients, and may lead to less than optimal outcomes for the patient. If the medically active agent is administered by injection, another injection increases the frequency of pain, the risk of infection, and the probability of an immune response in the patient. Thus, a need for medically active agents that have superior concentration profiles in the patient exists. The methods and compositions described herein provide solutions to these and other needs.

BRIEF SUMMARY

A medically active agent may be attached to a polyethylene glycol (PEG). The attachment of the polyethylene glycol may add molecular weight to the medically active agent and may lead to an increased half-life of the medically active agent. Additionally, the attachment of polyethylene glycol, including smaller PEG molecules, to a medically active agent may increase the hydrophobicity of the medically active agent and may make the medically active agent amphiphilic. The medically active agent may be more easily dissolved in an organic solvent with a biodegradable polymer. The biodegradable polymer may encapsulate the medically active agent in a microsphere. The encapsulation of the medically active agent may increase the half-life of the medically active agent. The formulations described herein may release the medically active agent slowly and uniformly over a period of time. The release profile may result in a sustained and near peak-less protein level over the intended treatment period, without the need of an excipient. The resulting concentration profile of the medically active agent in a patient may lead to a more optimal clinical result in the patient. Formulations described herein may be administered to a patient as infrequently as once a month.

In particular, site-specific modifications with hydrophilic proteins, may assist in administering a medically active agent to a patient. In one example, PEGylated insulin derivatives where the site of substitution is predominantly residue PheB1 (N-terminus of the B-chain) may be used. These derivatives may be physically and enzymatically more stable than native insulin. In addition, the derivatives may be more soluble in aqueous/organic systems than native insulin. Moreover, these derivatives may be less immunogenic and may have prolonged circulation half-lives. High yields of these site-specific PEGylated proteins may be possible with the methods described herein. These and other advantages may provide for a more effective method of treating diabetes or other afflictions. The higher yields may result in a more efficient, cost effective, and scalable manufacturing process.

Examples include a method of making a protein-PEG conjugate. The method may include providing an aqueous protein solution. The aqueous protein solution may include a protein, a pH buffer, and a chelating agent. The chelating agent may be chosen from the group consisting of an aminopolycarboxylic acid, a hydroxyaminocarboxylic acid, an N-substituted glycine, 2-(2-amino-2-oxocthyl) aminoethane sulfonic acid (BES), and deferoxamine (DEF). The method may also include introducing a boron-containing reducing agent and a methoxy polyethylene glycol aldehyde to the aqueous protein solution. The method may further include reacting the methoxy polyethylene glycol aldehyde with the protein to form the protein-PEG conjugate.

In some examples, the boron-containing reducing agent may be sodium cyanoborohydride. The sodium cyanoborohydride and the methoxy polyethylene glycol aldehyde may have a molar ratio ranging from about 5:1 to about 1.5:1. The pH buffer may maintain a pH of the aqueous protein solution ranging from 4.0 to 4.4 during the reaction. The pH may range from 3.8 to 4.0, from 4.0 to 4.2, or from 4.2 to 4.4 in examples.

In some examples, the boron-containing reducing agent may include dimethylamine borane ($Met_2NHBH_3$), trimethylamine borane ($Met_3NBH_3$), 2-picoline borane (2-methyl pyridine borane $C_6H_7NBH_3$), sodium triacetoxyborohydride ($NaBH(OAc)_3$), triethylamine borane ($Et_3NBH_3$), morpholine borane ($C_4H_9ONBH$), tert butylamine borane ($C_4H_{11}NBH_3$), or 5-ethyl-2-methyl-pyridine borane ($C_8H_{11}NBH_3$). These boron-containing reducing agents may not release cyanide gas during the reaction, which may be an advantage in manufacturing. The boron-containing reducing agent and the methoxy polyethylene glycol aldehyde may have a molar ratio ranging from about 25:1 to about 1.5:1. The pH buffer may maintain a pH of the aqueous protein solution ranging from 4.0 to 6.0 during the reaction. In some examples, the pH may range from 4.0 to 4.4, from 4.4 to 4.8, from 4.8 to 5.2, from 5.2 to 5.6, or from 5.6 to 6.0.

Examples may include a method of making an insulin-PEG conjugate. The method may include providing an aqueous insulin solution. The aqueous insulin solution may include an insulin, a pH buffer, an organic solvent, and a chelating agent. The chelating agent may include ethylenediaminetetraacetic acid (EDTA). The method may also include introducing a boron-containing reducing agent and a methoxy polyethylene glycol aldehyde to the aqueous insulin solution. The boron-containing reducing agent may be any boron-reducing agent described herein. The boron-containing reducing and methoxy polyethylene glycol aldehyde may have a molar ratio ranging from about 5:1 to about 1:1 or any molar ratio described herein. Furthermore, the method may include reacting the methoxy polyethylene glycol aldehyde with the insulin to form the insulin-PEG conjugate. The pH buffer may maintain a pH of the aqueous insulin solution in any range described herein during the reaction. The reaction of the methoxy polyethylene glycol aldehyde with the insulin may yield a PEG-PheB1-insulin conjugate at greater than 75% of all insulin-PEG conjugates produced.

Examples may include a method of making controlled-release microspheres containing a protein-PEG conjugate. The method may include providing an aqueous protein solution, which may include a protein, a pH buffer, and a chelating agent. The chelating agent may be chosen from the group consisting of an aminopolycarboxylic acid, a hydroxyaminocarboxylic acid, an N-substituted glycine, 2-(2-amino-2-oxocthyl) aminoethane sulfonic acid (BES), and deferoxamine (DEF). The method may also include introducing a boron-containing reducing agent and methoxy polyethylene glycol aldehyde to the aqueous protein solution. The boron-containing reducing agent may be any boron-containing reducing agent described herein. The boron-containing reducing agent and methoxy polyethylene glycol aldehyde may have any molar ratio described herein. The method may further include reacting the methoxy polyethylene glycol aldehyde with the protein to form the protein-PEG conjugate, where the pH buffer maintain a pH of the aqueous protein solution in a range from 4.0 to 6.0 during the reaction. Additionally, the method may include mixing the protein-PEG conjugate in an organic solvent with a biodegradable polymer. Furthermore, the method may include emulsifying the mixture of the protein-PEG conjugate and the biodegradable polymer in an aqueous solution. The method may include hardening emulsified mixture of the protein-PEG conjugate in the biodegradable polymer into the controlled-release microspheres.

BRIEF DESCRIPTION OF THE DRAWINGS

The present technology is described in conjunction with the appended figures.

DETAILED DESCRIPTION

Unaltered proteins may not have the desired concentration profiles and other favorable characteristics when used as medically active agents. PEGylation, the process of attaching polyethylene glycol (PEG) to a molecule, can aid in the administration of peptides and proteins, which may lead to improved pharmacological properties and increased effectiveness. PEG is a linear polymer composed of subunits of ethylene glycol and is soluble in both water and many organic solvents. PEG is flexible, biocompatible, and nontoxic. As a result of PEG properties, PEGylation increase half-life and/or solubility of a protein or peptide.

Conventional methods of producing site-specific protein-PEG conjugates may result in lower yields, perhaps only around 50%. Additionally, conventional methods may require more steps to protect proteins at less favorable sites or residues. Conventional methods may require proteins to undergo reaction steps in protein-adverse environments (high and low pH) for extended periods of time. These lower yields and more adverse environments may increase costs and decrease the clinical effectiveness of treatments.

Higher yields than yields through conventional methods of site-specific protein-PEG conjugates may be achieved. Polyethylene glycol aldehydes may provide more favorable yields than polyethylene glycol esters. The lower pH may aid specificity for the N-terminus of the pheB1 chain. Lower concentrations of sodium cyanoborohydride may be preferred because higher concentrations of the reducing agent may reduce the aldehyde on the PEG reagent. Concentrations or ratios of various components may be selected to maximize the yield of site-specific protein-PEG conjugates. These concentrations or ratios may be in a range that would not be predicted based on yield data from outside the range.

Figure 1:
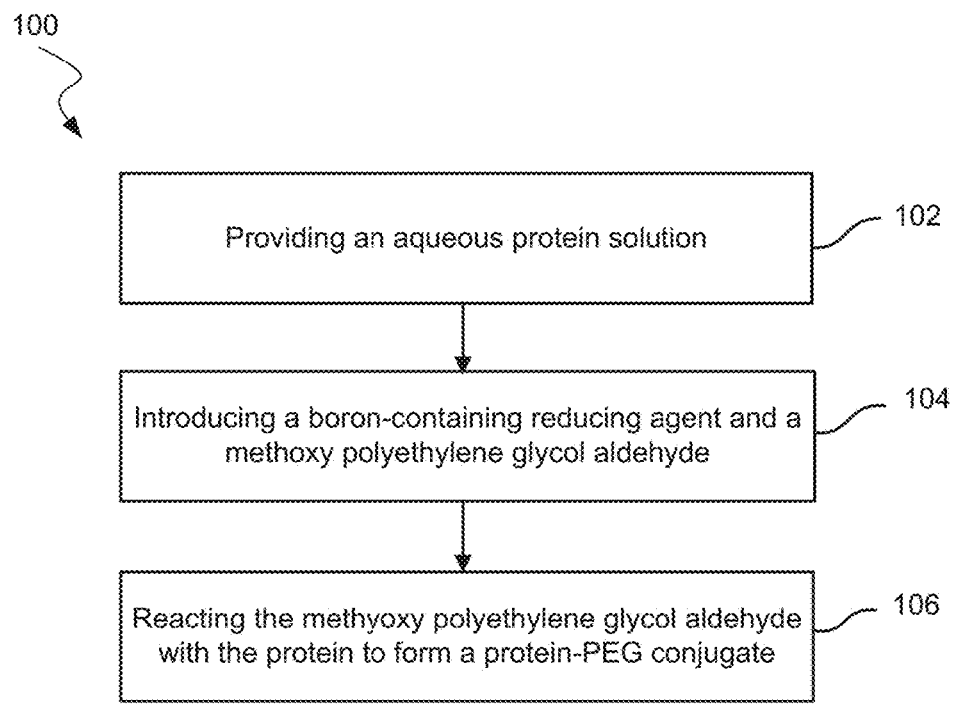
FIG. 1 shows a block diagram of a method of making a protein-PEG conjugate according to examples.

Examples include a method of making a protein-PEG conjugate, as shown in FIG. 1. Method 100 may include providing an aqueous protein solution 102. The aqueous protein solution may include a protein, a pH buffer, and a chelating agent. Additionally, the protein may be chosen from the group consisting of insulin, parathyroid hormone (PTH), a fragment of parathyroid hormone, growth hormone (e.g., human growth hormone (hGH)), glucagon-like peptide-1 (GLP-1), enfuvirtide (Fuzeon®), and octreotide (Sandostatin®). The insulin may include human insulin. The pH buffer may include an inorganic salt of phosphoric acid.

The chelating agent may be chosen from the group consisting of an aminopolycarboxylic acid, a hydroxyaminocarboxylic acid, an N-substituted glycine, 2-(2-amino-2-oxoethyl) aminoethane sulfonic acid (BES), and deferoxamine (DEF). The aminopolycarboxylic acid may be chosen from the group consisting of ethylenediaminetetraacetic acid (EDTA), diethylenetriamine pentaacetic acid (DTPA), nitrilotriacetic acid (NTA), N-2-acetamido-2-iminodiacetic acid (ADA), bis(aminoethyl)glycolether, N,N,N',N'-tetraacetic acid (EGTA), trans-diaminocyclohexane tetraacetic acid (DCTA), glutamic acid, and aspartic acid. The aminopolycarboxylic acid may exclude any one of these compounds or any group of these compounds. The hydroxyaminocarboxylic acid may be chosen from the group consisting of N-hydroxyethyliminodiacetic acid (HIMDA), N,N-bis-hydroxyethylglycine, and N-trishydroxymethylmethyl) glycine. The N-substituted glycine may include glycylglycine.

Method 100 may also include introducing a boron-containing reducing agent and a methoxy polyethylene glycol aldehyde 104 to the aqueous protein solution. The reducing agent may include sodium cyanoborohydride (NaCNBH$_3$), dimethylamine borane (Met$_2$NHBH$_3$), trimethylamine borane (Met$_3$NBH$_3$), 2-picoline borane (i.e., 2-methyl pyridine borane (C$_6$H$_7$NBH$_3$)), sodium triacetoxyborohydride (NaBH(OAc)$_3$), triethylamine borane (Et$_3$NBH$_3$), morpholine borane (C$_4$H$_9$ONBH), tert butylamine borane (C$_4$H$_{11}$NBH$_3$), or 5-ethyl-2-methyl-pyridine borane (C$_8$H$_{11}$NBH$_3$). The boron-containing reducing agent and the methoxy polyethylene glycol may have a molar ratio ranging from about 25:1 to about 1.5:1, from about 22:1 to about 5.5:1, from about 22:1 to about 1.6:1, or from about 10:1 to about 5.5:1 in examples.

The reducing agent may be sodium cyanoborohydride. Method 100 may also include introducing sodium cyanoborohydride and a methoxy polyethylene glycol aldehyde to the aqueous protein solution in some examples. The sodium cyanoborohydride and the methoxy polyethylene glycol aldehyde may have a molar ratio ranging from about 5:1 to about 1.5:1, from about 4:1 to about 1.5:1; from about 5:1 to about 2:1; or from about 5:1 to about 3:1 in examples.

Furthermore, method 100 may not include reacting a polyethylene glycol ester with the protein. A polyethylene glycol aldehyde may be selective for primary amines, while the polyethylene glycol ester may react with other functionalities and amino acids. The polyethylene glycol esters may require a higher pH for a reaction than for polyethylene glycol aldehydes.

Method 100 may further include reacting the methoxy polyethylene glycol aldehyde with the protein to form the protein-PEG conjugate 106. The reaction between aldehyde and amino groups may result in an imine intermediate. These reactions may be acid catalyzed and pH dependent. Insulin may have three amino groups available for PEGylation. Each may have a different pK$_a$ value. The lysine side chain may have a pK$_a$ of 10.5, the glycine N-terminus may have a pK$_a$ of 9.78, and the phenylalanine N-terminus may have a pK$_a$ of 9.31. The pH may affect the amino selectivity for reaction with an aldehyde. The pH buffer may maintain a pH of the aqueous protein solution ranging from 4.0 to 6.0 during the reaction. With cyanoborohydride as the reducing agent, the pH may range from 4.0 to 4.4 during the reaction.

The reaction of the methoxy polyethylene glycol aldehyde with the protein may yield a site-specific mono-PEGylated protein-PEG conjugate at greater than 75%, greater than 85%, or greater than 90% of all protein-PEG conjugates produced according to examples. For example, the protein may include insulin and the site-specific mono-PEGylated protein-PEG conjugate may include PEG-PheB 1-insulin conjugate. Reacting the methoxy polyethylene glycol may occur in the absence of agitation. Reacting the methoxy polyethylene glycol may exclude steps of protecting one or both of residues GlyA1 and LysB29. Sodium chloride or other salts that may increase conductivity of the mixture may not be added until after the reaction is completed or substantially completed.

Figure 2:
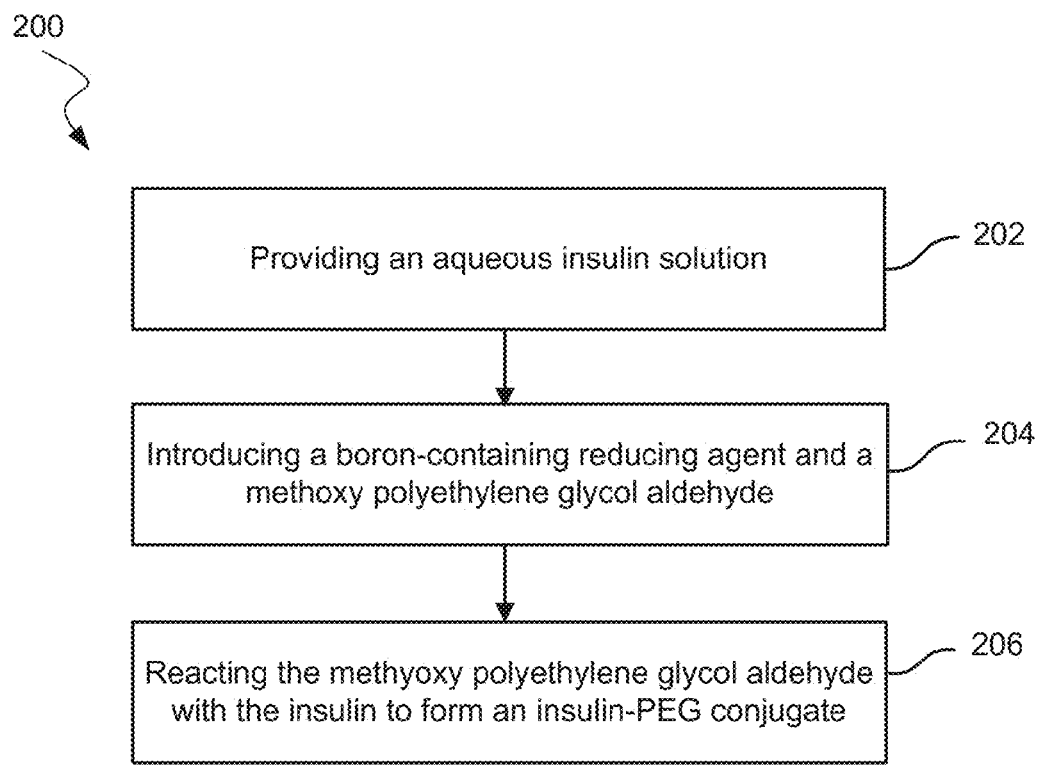
FIG. 2 shows a block diagram of a method of making an insulin-PEG conjugate according to examples.

As shown in FIG. 2, examples may include a method 200 of making an insulin-PEG conjugate. Method 200 may include providing an aqueous insulin solution 202. The aqueous insulin solution may include an insulin, a pH buffer, an organic solvent, and a chelating agent. The chelating agent may include ethylenediaminetetraacetic acid (EDTA) or any chelating agent described herein. The organic solvent may be chosen from the group consisting of ethanol, methanol, dimethyl sulfoxide (DMSO), dioxane, acetonitrile, dimethylformamide (DMF), and N-methylpyrrolidone (NMP).

Method 200 may also include introducing a boron-containing reducing agent and a methoxy polyethylene glycol aldehyde 204 to the aqueous insulin solution. The boron-containing reducing agent may include any of the reducing agents described herein. The boron-containing reducing agent and the methoxy polyethylene glycol aldehyde may have any molar ratio described herein.

Furthermore, method 200 may include reacting the methoxy polyethylene glycol aldehyde with the insulin to form the insulin-PEG conjugate 206. The pH buffer may maintain a pH of the aqueous insulin solution in any range described herein during the reaction. In these or other examples, the pH of the aqueous insulin solution may be about 4.0 in the reaction or any pH range described herein. When the reaction starts, the methoxy polyethylene glycol aldehyde and insulin may have a molar ratio of about 10:1 to about 1:1, or about 8:1 to about 3:1, or about 6:1 to about 4:1, or about 5:1 to about 1:1 according to examples.

The reaction of the methoxy polyethylene glycol aldehyde with the insulin may yield a PEG-PheB1-insulin conjugate at greater than 75% or between 75% and 85% of all insulin-PEG conjugates produced according to examples.

Figure 3:
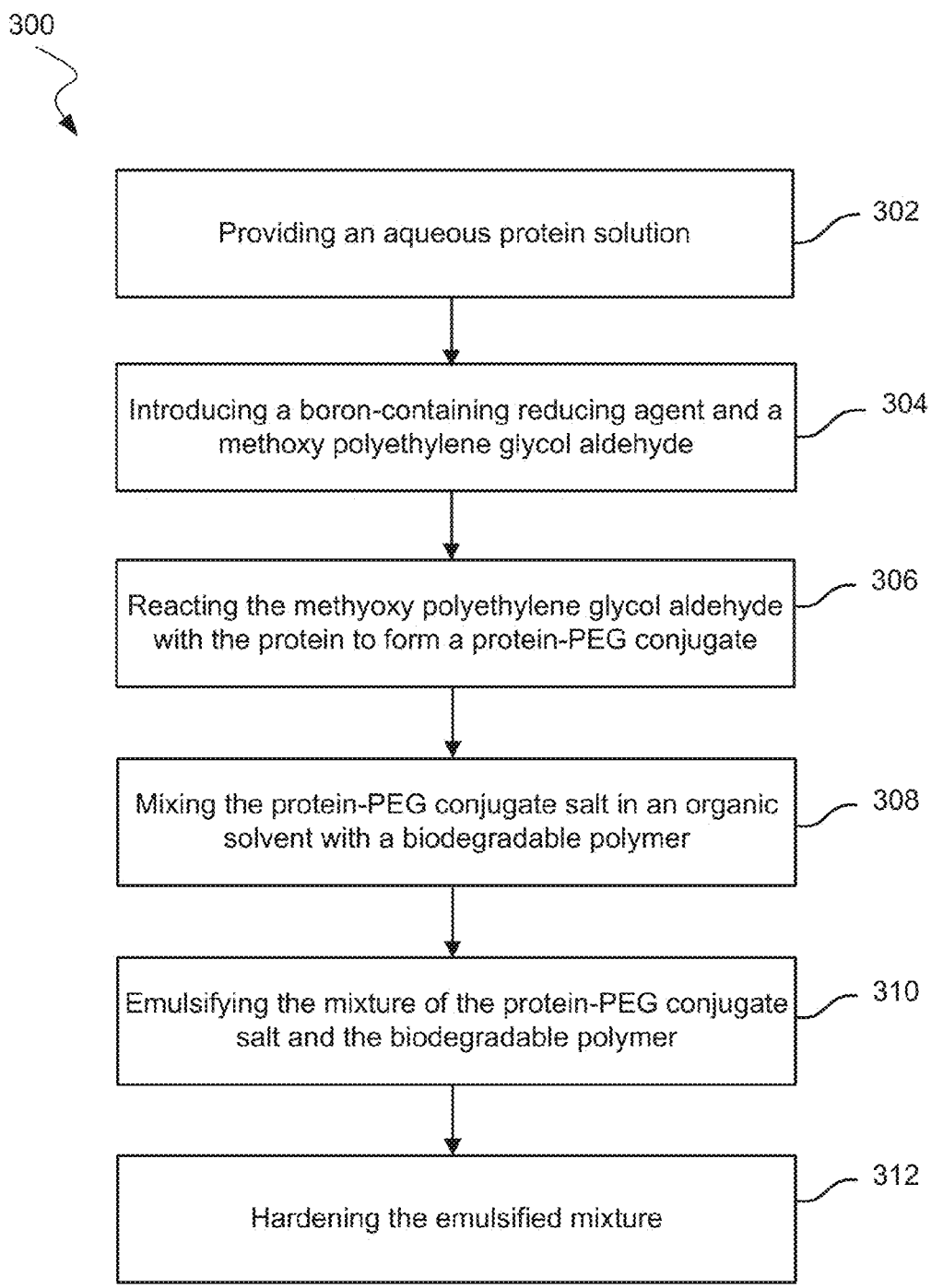
FIG. 3 shows a block diagram of a method of making controlled-release microspheres containing a protein-PEG conjugate according to examples.

As shown in FIG. 3, examples may include a method 300 of making controlled-release microspheres containing a protein-PEG conjugate. Method 300 may include providing an aqueous protein solution 302, which may include a protein, a pH buffer, and a chelating agent. The protein may be any of the proteins previously described. The pH buffer may be any pH buffer described herein. The chelating agent may be any chelating agent described herein.

Method 300 may also include introducing a boron-containing reducing agent and methoxy polyethylene glycol aldehyde 304 to the aqueous protein solution. The boron-containing reducing agent and methoxy polyethylene glycol aldehyde may have any molar ratio described herein.

Method 300 may further include reacting the methoxy polyethylene glycol aldehyde with the protein to form the protein-PEG conjugate 306, where the pH buffer maintains any pH range described herein during the reaction. The pH of the aqueous protein solution may be any pH described herein. Additionally, the protein-PEG conjugate may be a site-specific mono-PEGylated protein-PEG conjugate. The site-specific mono-PEGylated protein-PEG conjugate may include PEG-PheB 1-insulin conjugate. The PEG-PheB 1-insulin conjugate may have a yield of 75% to 85% or greater than 75% of all insulin-PEG conjugates produced according to examples.

Additionally, method 300 may include mixing the protein-PEG conjugate in an organic solvent with a biodegradable polymer 308. The organic solvent may include methylene chloride. The biodegradable polymer may be chosen from the group consisting of a polylactide, a polyglycolide; a poly(d,l-lactide-co-glycolide); a polycaprolactone; a polyorthoester; a copolymer of a polyester and a polyether; and a copolymer of polylactide and polyethylene glycol. The biodegradable polymer may exclude any polymer or any group of polymers described.

Furthermore, method 300 may include emulsifying the mixture of the protein-PEG conjugate and the biodegradable polymer 310 in an aqueous solution. Method 300 may include hardening the emulsified mixture 312 of the protein-PEG conjugate and the biodegradable polymer into the controlled-release microspheres.

EXAMPLE 1

Figure 4:
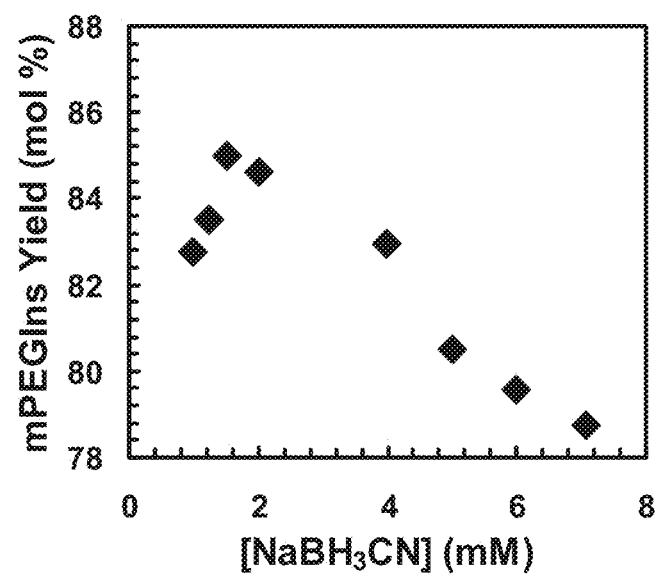
FIG. 4 shows a graph of the yield of monoPEGylated insulin as a function of the concentration of sodium cyanoborohydride according to examples.

Experiments are performed over a range of sodium cyanoborohydride concentrations ([NaBH$_3$CN]) in order to define operating conditions and limits of sodium cyanoborohydride for consistent monoPEGylated insulin-PEG conjugate ("mPEGIns") yields. The following parameters were held constant throughout the series of experiments (values in parentheses): [rhI]$_0$ (0.86 mM), [mPEGpropald]$_0$/[rhI]$_0$ (1.04), [EDTA]/[rhI]$_0$ (0.17-0.18), temperature (28° C.), buffer strength (30 mM), and pH (4.0). [rhI]$_0$ is the initial concentration of recombinant human insulin; [mPEGpropald]$_0$ is the initial concentration of methoxy propylene glycol aldehyde; [EDTA] is the concentration of ethylenediaminetetraacetic acid. Raw materials were also the same for each of the reactions. MonoPEGylated insulin-PEG conjugate yield is shown as a function of sodium cyanoborohydride in FIG. 4. At this value for [rhI]$_0$, mPEGIns yields show an optimal concentration between [NaBH$_3$CN]=1.0 mM and [NaBH$_3$CN]=1.5 mM. However, mPEGIns yield decreases at [NaBH$_3$CN] concentrations higher than 2 mM. The variation between mPEGIns yield with [NaBH$_3$CN]=1.0 mM and [NaBH$_3$CN]=1.5 mM is approximately 2 mol %. If the upper limit on [NaBH$_3$CN] is set to allow the same variation in mPEGIns yield, then an upper limit on [NaBH$_3$CN] may be set at 4.0 mM. The concentration of NaBH$_3$CN corresponding to the highest mPEGIns yield is observed to be 1.5 mM.

EXAMPLE 2

EDTA chelates Zn$^{2+}$ ions in the rhI raw material and, in doing so, solubilizes the rhI. In order to comply with United States Pharmacopeia (USP), rhI raw material must contain less than or equal to 1.00% (w/w) Zn$^{2+}$. Zn$^{2+}$ concentrations were simulated by replacing a small portion of sodium acetate in the reaction buffer with an appropriate amount of zinc acetate.

Figure 5A:
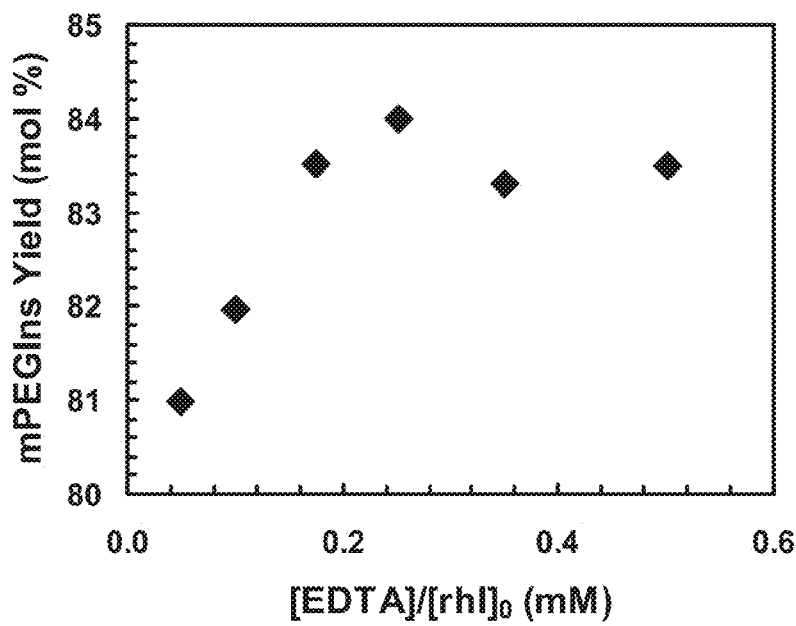
FIGS. 5A and 5B show graphs of the yields of monoPEGylated insulin as a function of the ratio of the concentration of a chelating agent to the initial concentration of insulin according to examples.

A narrow range of [EDTA]/[rhI]$_0$ was examined. The following parameters were held constant for this series of reactions (values in parentheses): [rhI]$_0$ (0.86-0.88 mM), [mPEGpropald]$_0$/[rhI]$_0$ (1.04), [NaBH$_3$CN] (1.2 mM), temperature (28° C.), buffer strength (30 mM), and pH (4.0). mPEGIns yield was monitored for each reaction by RPHPLC analysis, and this result is shown as a function of [EDTA]/[rhI]$_0$ in FIG. 5A. The data in FIG. 5A show a maximum mPEGIns yield at [EDTA]/[rhI]$_0$ of 0.25. The mPEGIns yield appears to fluctuate around 83.5 mol % for values of [EDTA]/[rhI]$_0$ greater than 0.175. Only a slight decrease in mPEGIns yield (~3 mol %) exists at [EDTA]/[rhI]$_0$ levels down to 0.05.

EXAMPLE 3

Figure 5B:
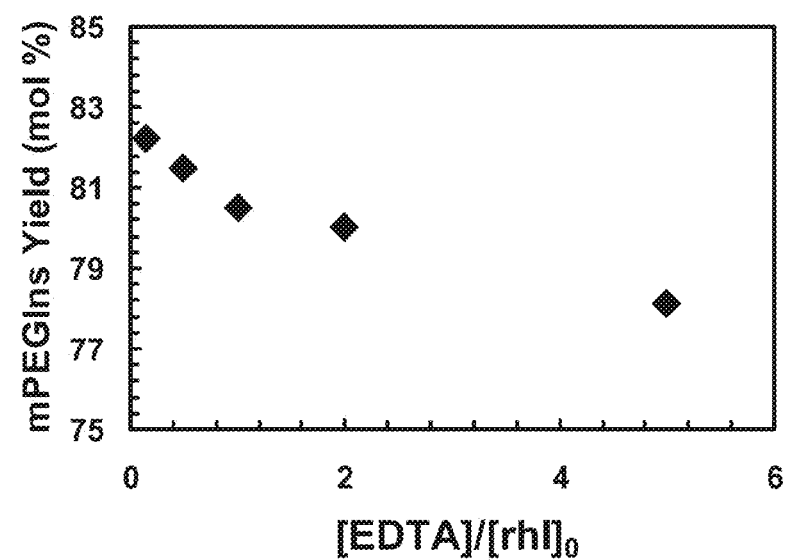

Example 2 was repeated for a larger range of [EDTA]/[rhI]$_0$. The following parameters were held constant for the repeat experiment (values in parentheses): [rhI]$_0$ (0.86 mM), [mPEGpropald]$_0$/[rhI]$_0$ (1.07), [NaBH$_3$CN] (2.0 mM), temperature (28° C.), buffer strength (40 mM), and pH (4.0). mPEGIns yield as a function of [EDTA]/[rhI]$_0$ is given for this set of experiments in FIG. 5B. Over the range shown in FIG. 5B, increasing [EDTA]/[rhI]$_0$ is observed to decrease mPEGIns yield.

The experiments in Examples 2 and 3 were completed with rhI containing 0.36% (w/w) Zn$^{2+}$. FIG. 5A shows that [EDTA]/[rhI]$_0$ in the range of 0.175 to 0.50 should result in approximately the same mPEGIns yield. In the context of Zn$^{2+}$ content, the corresponding range of [EDTA]/[Zn$^{2+}$] is from 0.55 to 1.56. [EDTA]/[Zn$^{2+}$]=0.55 for this case corresponds to [EDTA]/[rhI]$_0$=0.48. Based on the data in FIG. 5B, an upper end of the range for [EDTA]/[Zn$^{2+}$] may be 2.0. However, when reaction times are considered as in Example 8, an upper end of the range of [EDTA]/[Zn$^{2+}$] was observed to be 1.0.

EXAMPLE 4

Figure 6:
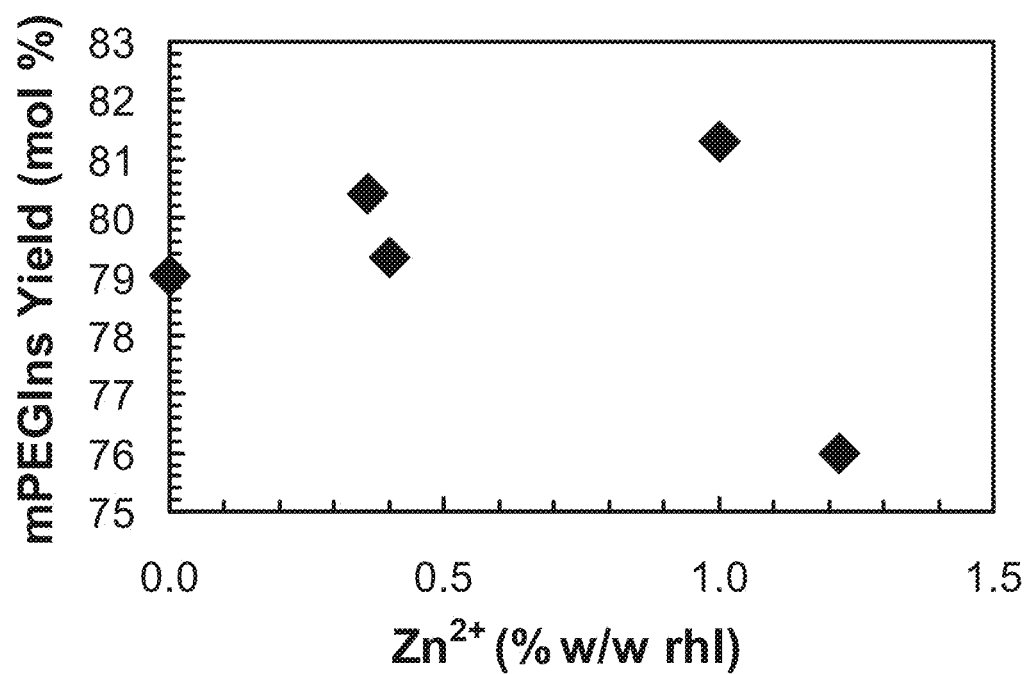
FIG. 6 shows a graph of the yield of monoPEGylated insulin as a function of zinc ion percentage according to examples.

The effect of rhI Zn$^{2+}$ content on mPEGIns yield was tested. Zinc acetate was added to reactions on recovered rhI to simulate 0.0% (w/w) Zn$^{2+}$ and 0.40% (w/w) Zn$^{2+}$. Zinc acetate was added to Diosynth rhI, lot #SIHR010-121306A with Zn$^{2+}$ content=0.36% (w/w), to simulate 0.36% (w/w), 1.00% (w/w), and 1.22% (w/w) Zn$^{2+}$. The following parameters were held constant for these experiments (values in parentheses): [rhI]$_0$ (0.86 mM), [mPEGpropald]$_0$/[rhI]$_0$ (1.05-1.07), [NaBH$_3$CN] (2.0 mM), temperature (28° C.), and pH (4.0). mPEGIns yield for these batches is shown as a function of Zn$^{2+}$ content for these batches in FIG. 6. The data in FIG. 6 are similar to data in FIGS. 5A and 5B. The value of [EDTA]/[rhI]$_0$ was set near the minimum value needed for consistent yield with Zn$^{2+}$=1.0% (w/w) in rhI, so the EDTA concentration would fail to meet that minimum somewhere between Zn$^{2+}$ contents of 1.0% (w/w) and 1.2% (w/w). As shown in FIG. 6, a relatively steep decline in mPEGIns yield appears from Zn$^{2+}$ between 1.0% (w/w) and 1.2% (w/w). A gradual decline in mPEGIns yield appears with Zn$^{2+}$ content decreasing from 1.00% (w/w) to 0.0% (w/w). This decline is similar to the effect shown in FIG. 5B—decreased mPEGIns yield with increasing EDTA per rhI/Zn$^{2+}$. In this example, a variation in Zn$^{2+}$ content between 0.0% (w/w) and 1.0% (w/w) was observed to result in a variation of mPEGIns yield of approximately 2.5 mol % in rhI.

EXAMPLE 5

Figure 7:
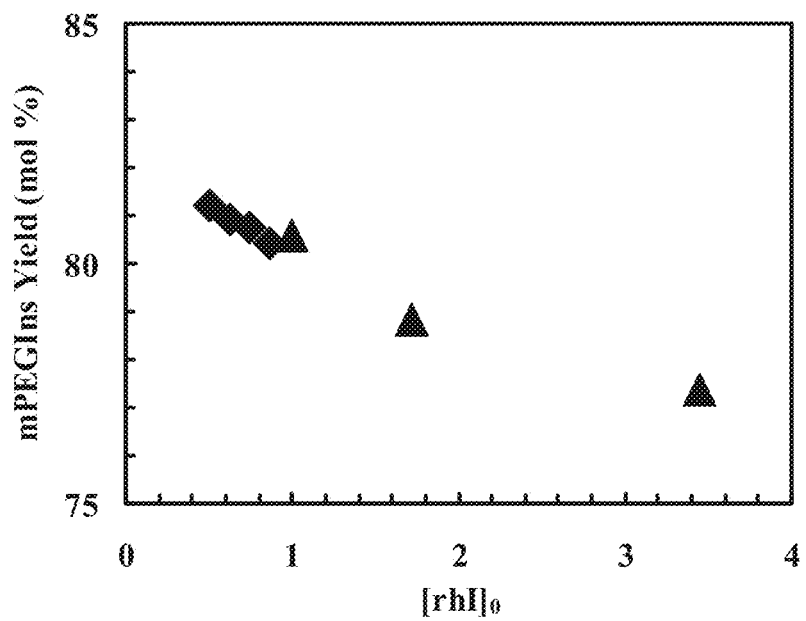
FIG. 7 shows a graph of the yield of monoPEGylated insulin as a function of the initial concentration of insulin according to examples.

Experiments for a range of [rhI]$_0$ were conducted. mPEGIns yield was once again monitored by RP-HPLC and is shown as a function of [rhI]$_0$ in FIG. 7. mPEGIns yield increased with each decrease in [rhI]$_0$. The increase in mPEGIns yield was only 0.8 mol % when [rhI]$_0$ was decreased from 0.86 mM to 0.50 mM. At some point, [rhI]$_0$ would become so low that the reaction will not proceed.

Based on the currently collected data, this critical $[rhI]_0$ may occur somewhere between $[rhI]_0=0.00$ mM and 0.50 mM.

The value of $[rhI]_0=0.86$ mM represents a concentration that corresponds to 50 g rhI in a 10 L reaction volume. Each decrease in $[rhI]_0$ corresponds to an increase in reactor volume if the batch size is held constant. Increased volume may result in larger masses of $NaBH_3CN$ to achieve the same concentration, as well as longer time requirements for mPEGIns purification by ion-exchange chromatography. Since the observed effect of $[rhI]_0$ on mPEGIns yield is small between 0.50 mM and 0.86 mM, and for the convenience and safety issues described above, a recommended set point for $[rhI]_0$ is 0.86 mM, with lower and upper limits of 0.50 mM and 1.0 mM, respectively.

EXAMPLE 6

Figure 8:
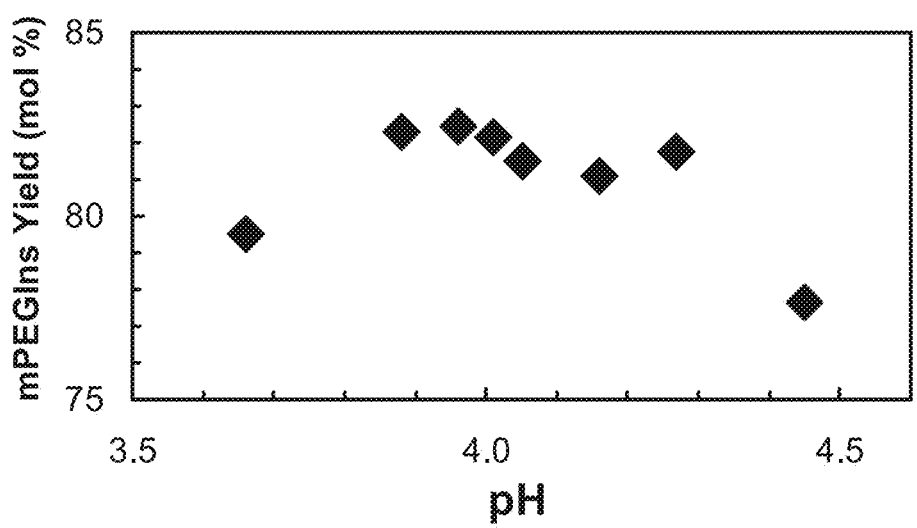
FIG. 8 shows a graph of the yield of monoPEGylated insulin as a function of pH according to examples.

Experiments were completed over a pH range. The following parameters were held constant throughout the series of experiments (values in parentheses): $[rhI]_0$ (0.86 mM), $[mPEGpropald]_0/[rhI]_0$ (1.04), $[NaBH_3CN]$ (2.0 mM), $[EDTA]/[rhI]_0$ (0.175), temperature (28° C.), and buffer strength (30 mM). mPEGIns yield is shown as a function of pH for these batches in FIG. 8. mPEGIns yield varied less than 1.5 mol % from minimum to maximum between pH=3.88 and pH=4.27. Values outside that range showed significantly more variation. A target value for pH may be 4.0, the approximate value of pH where mPEGIns yield was maximized.

EXAMPLE 7

Figure 9A:
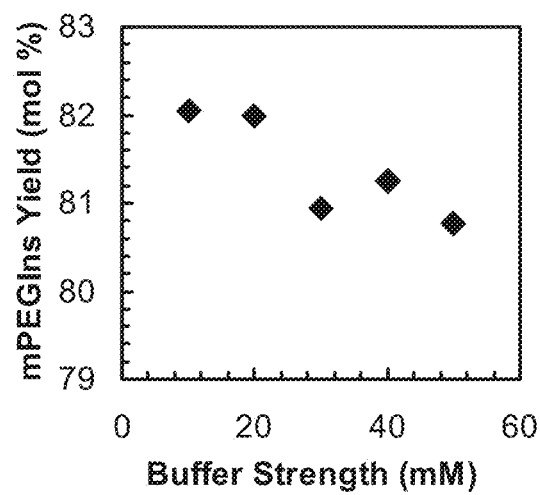
FIGS. 9A and 9B show graphs of the yield of monoPEGylated insulin as a function of buffer strength according to examples.
Figure 9B:
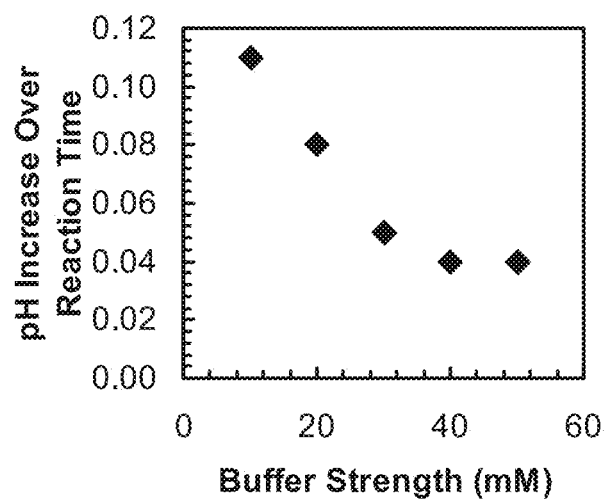

Experiments were completed with variations in acetate buffer strength. The following parameters were held constant throughout the series of experiments (values in parentheses): $[rhI]_0$ (0.86 mM), $[mPEGpropald]_0/[rhI]_0$ (1.07), $[NaBH_3CN]$ (2.0 mM), $[EDTA]/[rhI]_0$ (0.5), temperature (28° C.), and pH (4.0). mPEGIns yield is shown as a function of acetate buffer strength in FIG. 9A. A general trend appears to exist toward higher mPEGIns yield with lower buffer strength, but this trend affects mPEGIns yield to just over 1 mol % for buffer strengths between 10 mM and 50 mM. The pH of the reaction mixture was measured at the beginning and at the end of the reaction, and the change is shown as a function of acetate buffer strength in FIG. 9B. At buffer strengths greater than or equal to 40 mM, the change in pH over the course of the reaction appears to have reached a plateau. To limit pH variation within 0.1 pH unit, the lower limit on buffer strength may be set at 20 mM. To consistently limit reaction pH from batch to batch, the target value of buffer strength may be at 30 mM.

EXAMPLE 8

Figure 10:
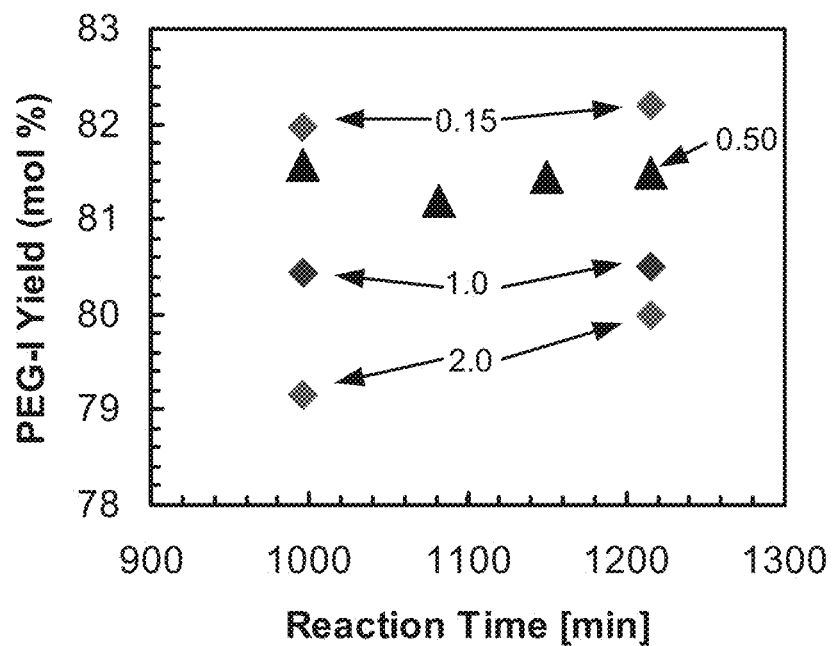
FIG. 10 shows a graph of the yield of monoPEGylated insulin as a function of reaction time for various ratios of the concentration of a chelating agent to the initial concentration of insulin according to examples.

From previous data, rhI conversion and mPEGIns yield increased significantly between approximately 3 hours and 20 hours. An experiment was performed in which samples were taken at various reaction times, including at 16.6 h, 18.0 h, 19.2 h, and 20.3 h. $[EDTA]/[rhI]_0$ was varied at 0.15, 0.50, 1.0, and 2.0. This experiment fixed the following parameter values: $[rhI]_0=0.86$ mM, $[mPEGpropald]_0/[rhI]_0=1.07$, $[NaBH_3CN]=2.0$ mM, temperature=28° C., buffer strength=30 mM, and pH=4.0. mPEGIns yield is shown for each of these four batches as a function of reaction time in FIG. 10. The labels in FIG. 10 indicate the different values of $[EDTA]/[rhI]_0$. The mPEGIns yield for $[EDTA]/[rhI]_0=0.50$ varies slightly among time points between 16.6 h and 20.3 h. Because it is unlikely that the mPEGIns yield decreases with increased reaction time, the variation likely represents measurement and analysis variation rather than real changes in mPEGIns yield. For $[EDTA]/[rhI]_0=0.50$, the data in FIG. 10 show that between a reaction time of 16.6 h and a maximum reaction time of 20.3 h, a longer reaction time results in no additional benefit to mPEGIns yield beyond 16.6 h. The same trend (approximately no change between 16.6 h and 20.3 h) also appears to exist with $[EDTA]/[rhI]_0=0.15$ and 1.0 but not for $[EDTA]/[rhI]_0=2.0$. At $[EDTA]/[rhI]_0=2.0$, mPEGIns yield increased by approximately 1 mol % between 16.6 h and 20.3 h. In order to reach a plateau in mPEGIns yield at 16.6 h, the upper limit for $[EDTA]/[rhI]_0$ was observed to be 1.0.

EXAMPLE 9

Figure 11:
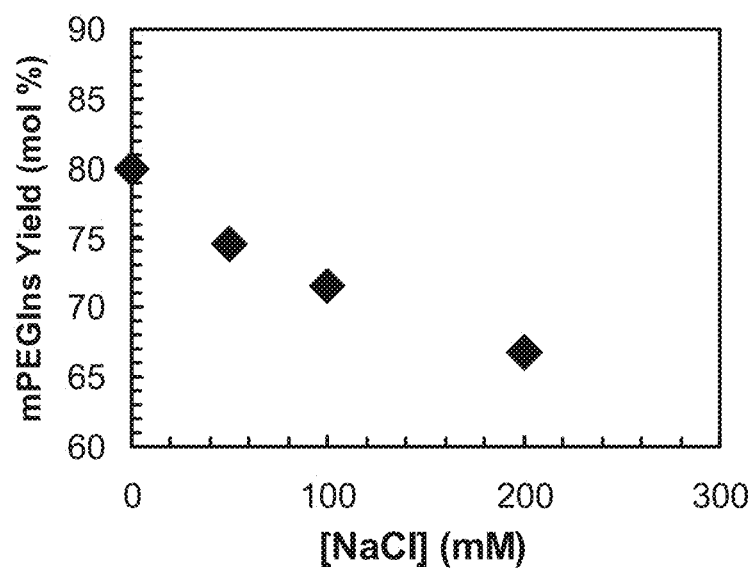
FIG. 11 shows a graph of the yield of monoPEGylated insulin as a function sodium chloride concentration according to examples.

The effect of varying NaCl concentration in the mPEGIns reaction mixture on the mPEGIns yield was tested. The following parameters were held constant throughout the series of experiments (values in parentheses): $[rhI]_0$ (0.86 mM), $[mPEGpropald]_0/[rhI]_0$ (1.05), $[NaBH_3CN]$ (1.5 mM), $[EDTA]/[rhI]_0$ (0.5), temperature (28° C.), buffer strength (30 mM), and pH (4.0). mPEGIns yield is shown as a function of [NaCl] in FIG. 11. Conversion of rhI mirrored the trend seen in mPEGIns yield data (not shown). At [NaCl] levels at or above 100 mM, precipitate was noticeably present in the reaction mixture prior to addition of $NaBH_3CN$ (not shown). From this example, mPEGIns yield was reduced by the presence of NaCl even at 50 mM, and as a result, NaCl additions to control solution conductivity may be delayed until post-reaction.

EXAMPLE 10

PEGylation experiments were performed with 2-methyl pyridine borane with the following parameters being held constant (values in parentheses): $[rhI]_0$ (0.86 mM), $[mPEGpropald]_0/[rhI]_0$ (1.05), [2-methyl pyridine borane] (1.5 mM), $[EDTA]/[rhI]_0$ (0.5), temperature (28° C.), acetate buffer strength (30 mM), and pH (4.0). The PEGylation efficiency was determined by RP-HPLC to be 55% monoPEGylation on the insulin B-chain with no detectable monoPEGylation of the n-terminus of the insulin A-chain.

EXAMPLE 11

Figure 12:
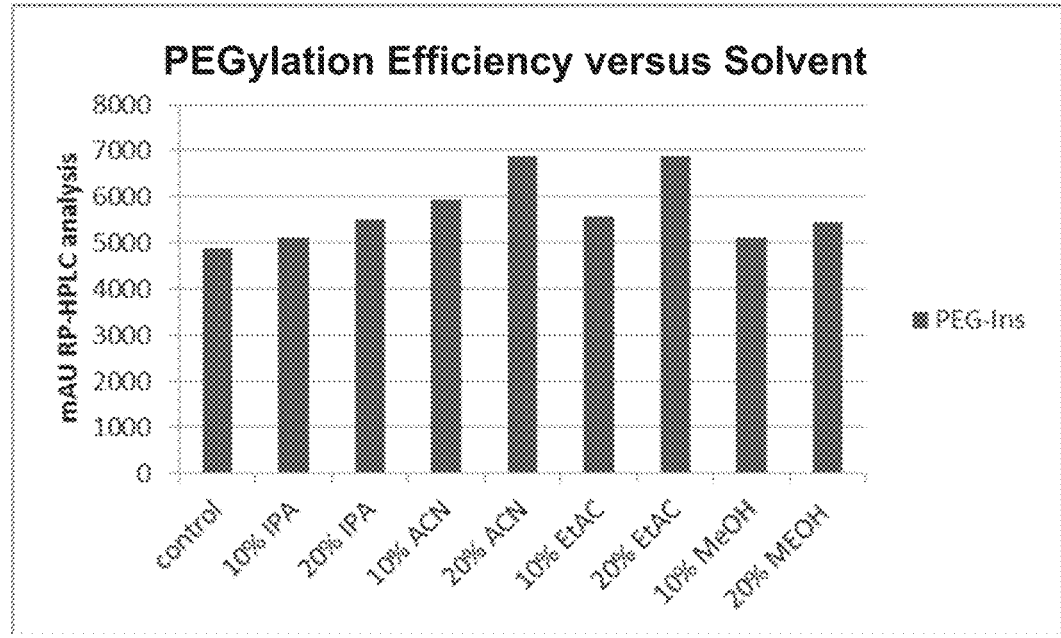
FIG. 12 shows a graph of PEGylation efficiency versus solvent according to examples.

The effects of solvent addition on PEGylation efficiency were evaluated with the following parameters being held constant: $[rhI]_0$ (0.86 mM), $[mPEGpropald]_0/[rhI]_0$ (1.05), [2-methyl pyridine borane] (20 mM), $[EDTA]/[rhI]_0$ (0.5), temperature (28° C.), and pH 4 acetate buffer strength (30 mM). The results shown in FIG. 12 indicate that acetonitrile (ACN) and ethyl acetate (EtAC) have beneficial effects on PEGylation yields, presumably due to enhanced insulin solubility. Also shown in FIG. 12 are isopropanol (IPA) and methanol (MeOH).

EXAMPLE 12

Figure 13:
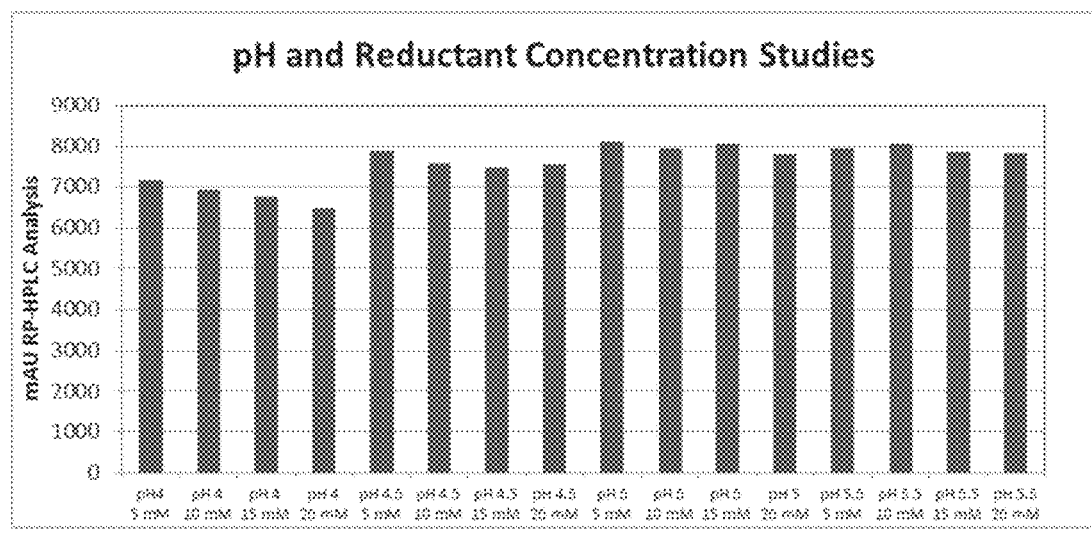
FIG. 13 shows a graph of PEGylation efficiency for different pHs and reducing agent concentrations according to examples.

The effects of pH and 2-methyl pyridine borane concentration on the PEGylation efficiency were evaluated with the following parameters being held constant: $[rhI]_0$ (0.86 mM), $[mPEGpropald]_0/[rhI]_0$ (1.05), $[EDTA]/[rhI]_0$ (0.5), temperature (28° C.), acetonitrile (20%), and acetate buffer strength (30 mM). RP-HPLC analysis was used to determine PEG-insulin concentrations in the reaction mixtures. The results as shown in FIG. 13 indicate an optimum at around pH 5 when using 5 mM 2-methyl pyridine borane as the reductant.

EXAMPLE 13

Figure 14:
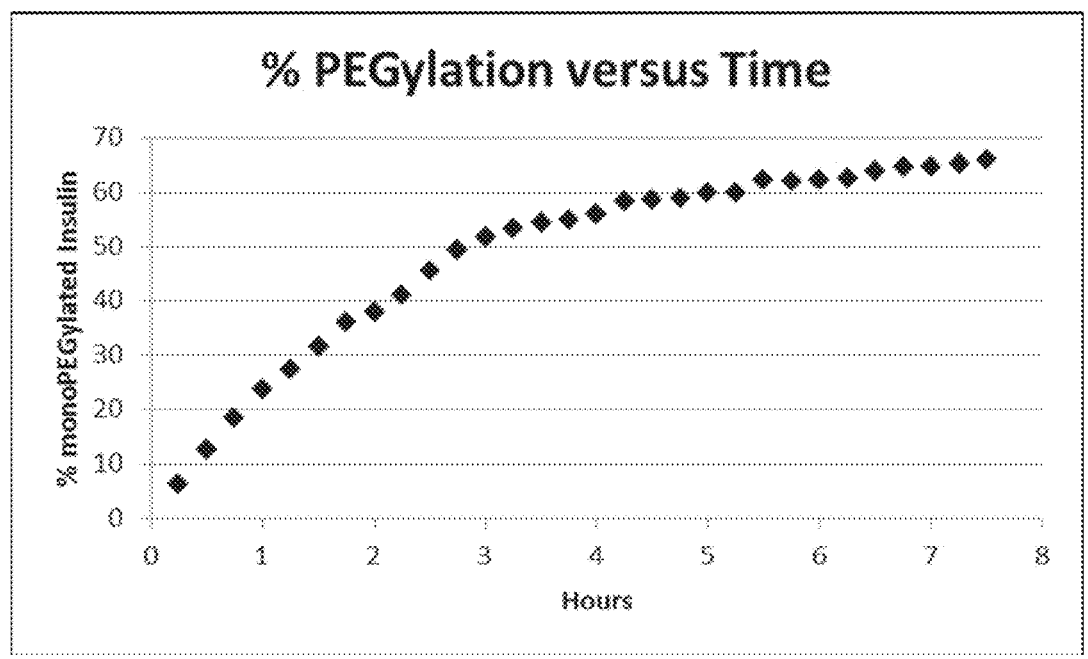
FIG. 14 shows a graph of the percentage of monoPEGylated insulin versus time according to examples.

The rate of insulin PEGylation was evaluated with the following parameters being held constant: $[rhI]_0$ (0.86 mM), $[mPEGpropald]_0/[rhI]_0$ (1.05), [2-methyl pyridine borane] (5 mM), $[EDTA]/[rhI]_0$ (0.5), temperature (28° C.), 20% acetonitrile, and pH 5 acetate buffer strength (30 mM). RP-HPLC analysis was used to determine PEG-insulin concentrations in the reaction mixture. The percent of monoPEGylated insulin over time is shown in FIG. 14. The reaction was allowed to proceed for 16 hours, at which point, the percent of monoPEGylation was around 75% and considered complete.

EXAMPLE 14

Figure 15:
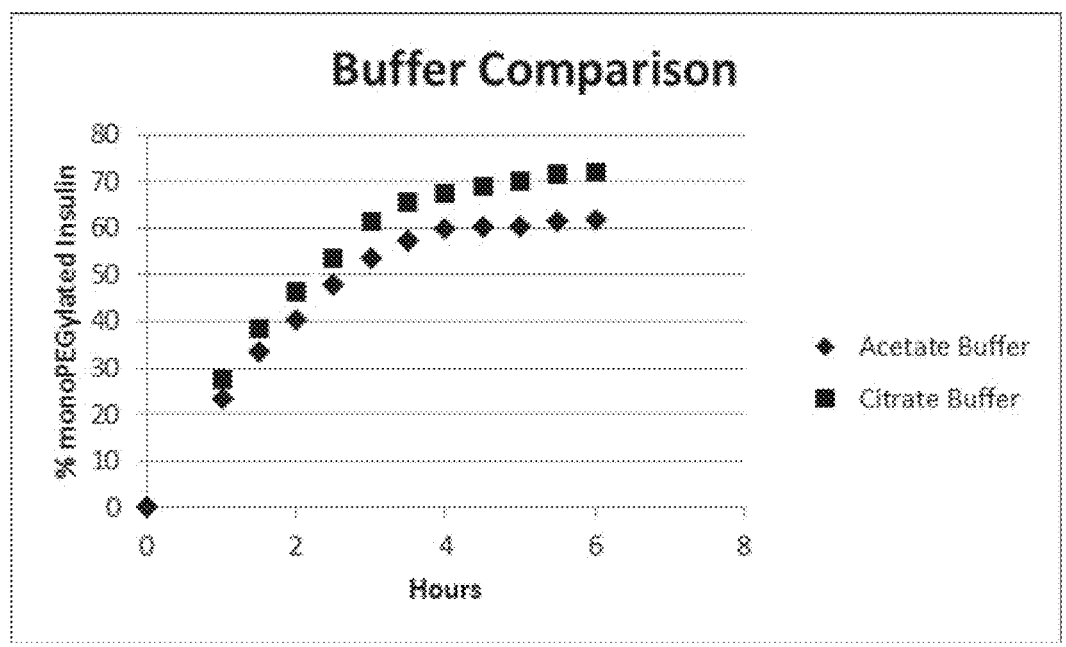
FIG. 15 shows a comparison of acetate and citrate buffers on monoPEGylated insulin yields according to examples.

The effects of the buffering agent composition on rate of PEGylation was evaluated with the following parameters being held constant: $[rhI]_0$ (0.86 mM), $[mPEGpropald]_0/[rhI]_0$ (1.05), [2-methyl pyridine borane] (5 mM), $[EDTA]/[rhI]_0$ (0.5), temperature (28° C.), 20% acetonitrile and pH 5 buffer strength (30 mM). The results are shown in FIG. 15. RP-HPLC analysis was used to determine PEG-insulin concentrations in the reaction mixture. The acetate buffer shows higher yields than the citrate buffer.

EXAMPLE 15

Figure 16:
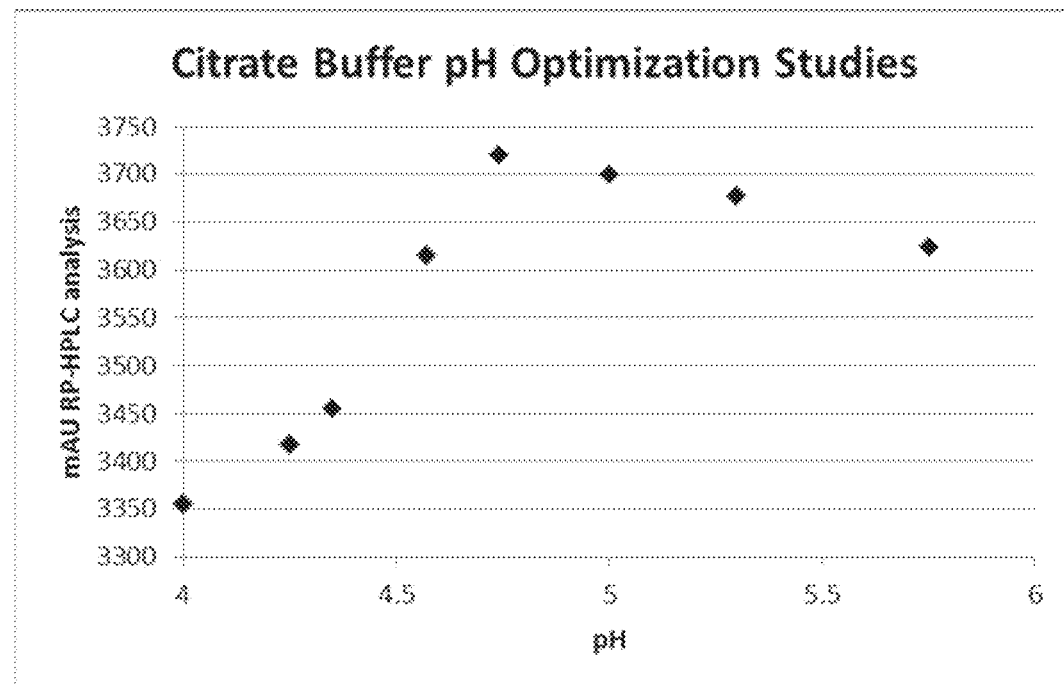
FIG. 16 shows a graph of the effects of the pH of a citrate buffer on PEGylation efficiency according to examples.

The effects of the pH of the citrate buffer on PEGylation efficiency was evaluated with the following parameters being held constant: $[rhI]_0$ (0.86 mM), $[mPEGpropald]_0/[rhI]_0$ (1.05), [2-methyl pyridine borane] (5 mM), $[EDTA]/[rhI]_0$ (0.5), temperature (28° C.), 20% acetonitrile, and citrate buffer strength (30 mM). RP-HPLC analysis was used to determine PEG-insulin concentrations in the reaction mixtures after 3 hours, as shown in FIG. 16.

EXAMPLE 16

The effects of replacing 5 kDa mPEG propyladehyde with 5 kDa mPEG NHS ester was evaluated with the following reaction parameters : $[rhI]_0$ (0.86 mM), $[mPEG-NHS ester]_0/[rhI]_0$ (1.05), $[EDTA]/[rhI]_0$ (0.5), temperature (28° C.), and 100 mM sodium phosphate pH 6.5). RP-HPLC analysis at 30 min and 1 hour indicated that the reaction had ended with approximately 72% of the starting insulin remaining underivatized, 23% PEGylation of the N-terminus of the B-chain, and 5% other PEGylated forms of insulin. This example shows that mPEG NHS ester is less effective than the mPEG propyladehyde in PEGylating the N-terminus of the B-chain of insulin.

EXAMPLE 17

PEGylation experiments were performed with Glucagon-like Peptide 1 (GLP-1) with the following reaction conditions $[GLP-1]_0$ (1-2.5 mg/mL), $[mPEGpropald]_0/[GLP-1]_0$ (1.2), $[NaCNBH_3]$ (5 mM), temperature (25° C.), acetate buffer strength (10 mM), and pH (4.5). After 16 hours, the PEGylation reactions were analyzed by RP-HPLC. MonoP-EGylation of GLP-1 was observed at 90-95% with 5-10% unreacted GLP-1 and 1-2% diPEGylation. The monoPEGy- lated GLP-1 was purified using cation exchange chromatography, buffer exchanged into 0.02% ammonium bicarbonate, and freeze dried. Microparticles containing the PEG-GLP-1 conjugate were prepared using an o/w single-emulsion solvent extraction/evaporation process. The oil phase consisted of 8.5% (w/v) PLGA polymer and 5 mg/mL of PEG-GLP-1 dissolved in $MeCl_2$. The oil phase was emulsified using vortexing with a 2.5×volume excess of 1% w/v. Polyvinyl alcohol (PVA) and the primary emulsion was added to a 15×excess of 0.3% PVA stirring at 300 rpm. Then a 30×excess of 2% isopropanol (IPA) was added approximately 10 minutes later, and the suspension was stirred to facilitate microsphere hardening via solvent evaporation. After 3 hours, the hardened microspheres were filtered, washed with a large volume of double distilled $H_2O$, and freeze dried.

EXAMPLE 18

PEGylation experiments were performed with parathyroid hormone (PTH 1-34) with the following reaction conditions $[PTH]_0$ (2.5 mg/mL), $[mPEGpropald]_0/[PTH]_0$ (1.2), $[NaCNBH_3]$ (20 mM), temperature (25° C.), acetate buffer strength (30 mM), and pH (4.5). After 16 hours, the PEGylation reaction was analyzed by RP-HPLC. MonoP-EGylation of PTH was observed at 68% with 24% unreacted PTH and 8% other PEGylation. The monoPEGylated PTH was purified using cation exchange chromatography, buffer exchanged into 0.02% ammonium bicarbonate, and freeze dried. Microparticles containing the PEG-PTH conjugate were prepared using an o/w single-emulsion solvent extraction/evaporation process. The oil phase consisted of 8.5% (w/v) PLGA polymer and 1 mg/mL of PEG-PTH dissolved in $MeCl_2$. The oil phase was emulsified using vortexing with a 2.5×volume excess of 1% w/v PVA, and the primary emulsion was added to a 15×excess of 0.3% PVA stifling at 300 rpm. Then a 30× excess of 2% IPA was added approximately 10 minutes later, and the suspension was stirred to facilitate microsphere hardening via solvent evaporation. After 3 hours, the hardened microspheres were filtered, washed with a large volume of double distilled $H_2O$ and freeze dried.

EXAMPLE 19

PEGylation experiments were performed with human growth hormone (hGH) with the following reaction conditions: $[hGH]_0$ (2.5 mg/mL), $[mPEGpropald]_0/[hGH]_0$ (3), $[NaCNBH_3]$ (20 mM), temperature (25° C.), acetate buffer strength (30 mM), and pH (5.5). After 16 hours, the PEGylation reaction was analyzed by RP-HPLC. MonoPEGylation of hGH was observed at 65% with 30% unreacted hGH and 5% other PEGylation. The monoPEGylated hGH was purified using anion exchange chromatography, buffer exchanged into 0.02% ammonium bicarbonate, and freeze dried. Microparticles containing the PEG-hGH conjugate were prepared using an o/w single-emulsion solvent extraction/evaporation process. The oil phase consisted of 8.5% (w/v) PLGA polymer and 5 mg/mL of PEG-hGH dissolved in $MeCl_2$. The oil phase was emulsified using vortexing with a 2.5×volume excess of 1% w/v PVA, and the primary emulsion was added to a 15×excess of 0.3% PVA stifling at 300 rpm. Then a 30×excess of 2% IPA was added approximately 10 minutes later, and the suspension was stirred to facilitate microsphere hardening via solvent evaporation.

After 3 hours, the hardened microspheres were filtered, washed with a large volume of double distilled H$_2$O, and freezer dried.

In this description, for the purposes of explanation, numerous details have been set forth in order to provide an understanding of various examples of the present technology. It will be apparent to one skilled in the art, however, that certain examples may be practiced without some of these details, or with additional details.

Having described several examples, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific example may not always be present in variations of that example or may be added to other examples.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the protein" includes reference to one or more proteins and equivalents thereof known to those skilled in the art, and so forth. The invention has now been described in detail for the purposes of clarity and understanding. However, it will be appreciated that certain changes and modifications may be practice within the scope of the appended claims.

What is claimed is:

1. A method of making a protein-PEG conjugate, the method comprising:
   providing an aqueous protein solution comprising a protein, a pH buffer, and a chelating agent, wherein:
   the protein is insulin,
   the pH buffer is an acetate or a citrate, and
   the chelating agent is chosen from the group consisting of an aminopolycarboxylic acid, a hydroxyaminocarboxylic acid, an N-substituted glycine, 2-(2-amino-2-oxocthyl) aminoethane sulfonic acid (BES), and deferoxamine (DEF);
   introducing boron-containing reducing agent and a methoxy polyethylene glycol aldehyde to the aqueous protein solution, wherein the boron-containing reducing agent and methoxy polyethylene glycol aldehyde have a molar ratio ranging from about 25:1 to about 1.5:1; and
   reacting the methoxy polyethylene glycol aldehyde with the protein to form the protein-PEG conjugate, wherein:
   the pH buffer maintains a pH of the aqueous protein solution ranging from 3.88 to 4.27 during the reaction, and
   the reaction of the methoxy polyethylene glycol aldehyde with the protein yields a mono-PEGylated protein-PEG conjugate.

2. The method of claim 1, wherein the boron-containing reducing agent is selected from the group consisting of sodium cyanoborohydride, dimethylamine borane, trimethylamine borane, 2-methyl pyridine borane, sodium triacetoxyborohydride, triethylamine borane, morpholine borane, tert butylamine borane, and 5-ethyl-2-methyl-pyridine borane.

3. The method of claim 1, wherein the boron-containing reducing agent is 2-methyl pyridine borane.

4. The method of claim 1, wherein the mono-PEGylated protein-PEG conjugate comprises PEG-PheB1-insulin conjugate.

5. The method of claim 1, wherein the chelating agent is the aminopolycarboxylic acid selected from the group consisting of ethylenediaminetetraacetic acid (EDTA), diethylenetriamine pentaacetic acid (DTPA), nitrilotriacetic acid (NTA), N-2-acetamido-2-iminodiacetic acid (ADA), bis (aminoethyl)glycolether, N,N,N',N'-tetraacetic acid (EGTA), trans-diaminocyclohexane tetraacetic acid (DCTA), glutamic acid, and aspartic acid.

6. The method of claim 1, wherein the chelating agent is the aminopolycarboxylic acid, and the aminopolycarboxylic acid is ethylenediaminetetraacetic acid (EDTA).

7. The method of claim 1, wherein the hydroxyaminocarboxylic acid is chosen from the group consisting of N-hydroxyethyliminodiacetic acid (HIMDA), N,N-bis-hydroxyethylglycine, and N-trishydroxymethylmethyl) glycine.

8. The method of claim 1, wherein the N-substituted glycine comprises glycylglycine.

9. A method of making an insulin-PEG conjugate, the method comprising:
   providing an aqueous insulin solution comprising an insulin, a pH buffer, an organic solvent, and a chelating agent comprising ethylenediaminetetraacetic acid (EDTA);
   introducing a boron-containing reducing agent and a methoxy polyethylene glycol aldehyde to the aqueous insulin solution, wherein the boron-containing reducing agent and methoxy polyethylene glycol aldehyde have a molar ratio ranging from about 25:1 to about 1.5:1; and
   reacting the methoxy polyethylene glycol aldehyde with the insulin to form the insulin-PEG conjugate, wherein:
   the pH buffer maintains a pH of the aqueous insulin solution in a range from 3.88 to 4.27 during the reaction,
   the pH buffer is an acetate or a citrate, and
   the reaction of the methoxy polyethylene glycol aldehyde with the insulin yields a mono-PEGylated insulin-PEG conjugate.

10. The method of claim 9, wherein the boron-containing reducing agent is selected from the group consisting of sodium cyanoborohydride, dimethylamine borane, trimethylamine borane, 2-methyl pyridine borane, sodium triacetoxyborohydride, triethylamine borane, morpholine borane, tert butylamine borane, and 5-ethyl-2-methyl-pyridine borane.

11. The method of claim 9, wherein the boron-containing reducing agent is 2-methyl pyridine borane.

12. The method of claim 9, wherein the methoxy polyethylene glycol aldehyde and the insulin have a molar ratio of about 10:1 to about 1:1 when the reaction starts.

13. The method of claim 9, wherein the boron-containing reducing agent and methoxy polyethylene glycol aldehyde have a molar ratio ranging from about 22:1 to about 5.5:1.

14. The method of claim 9, wherein the organic solvent is chosen from the group consisting of ethanol, methanol, dimethyl sulfoxide (DMSO), dioxane, acetonitrile, dimethylformamide (DMF), and N-methylpyrrolidone (NMP).

15. The method of claim 9, wherein the organic solvent is dioxane.

16. The method of claim 9, wherein the insulin comprises human insulin.

17. A method of making controlled-release microspheres containing a protein-PEG conjugate, the method comprising:
   providing an aqueous protein solution comprising a protein, a pH buffer, and a chelating agent, wherein:
      the protein is insulin,
      the pH buffer is an acetate or a citrate, and
      the chelating agent is chosen from the group consisting of an aminopolycarboxylic acid, a hydroxyaminocarboxylic acid, an N-substituted glycine, 2-(2-amino-2-oxocthyl) aminoethane sulfonic acid (BES), and deferoxamine (DEF);
   introducing a boron-containing reducing agent and a methoxy polyethylene glycol aldehyde to the aqueous protein solution, wherein the boron-containing reducing agent and methoxy polyethylene glycol have a molar ratio ranging from about 25:1 to about 1.5:1;
   reacting the methoxy polyethylene glycol aldehyde with the protein to form the protein-PEG conjugate, wherein the pH buffer maintains a pH of the aqueous protein solution ranging from 3.88 to 4.27 during the reaction;
   mixing the protein-PEG conjugate in an organic solvent with a biodegradable polymer to form a mixture;
   emulsifying the mixture of the protein-PEG conjugate and the biodegradable polymer in an aqueous solution to form an emulsified mixture; and
   hardening the emulsified mixture of the protein-PEG conjugate and the biodegradable polymer into the controlled-release microspheres, and
      the reaction of the methoxy polyethylene glycol aldehyde with the protein yields a mono-PEGylated protein-PEG conjugate.

18. The method of claim 17, wherein the boron-containing reducing agent is selected from the group consisting of sodium cyanoborohydride, dimethylamine borane, trimethylamine borane, 2-methyl pyridine borane, sodium triacetoxyborohydride, triethylamine borane, morpholine borane, tert butylamine borane, and 5-ethyl-2-methyl-pyridine borane.

19. The method of claim 17, wherein the boron-containing reducing agent is 2-methyl pyridine borane.

20. The method of claim 18, wherein the mono-PEGylated protein-PEG conjugate comprises PEG-PheB1-insulin conjugate.

21. The method of claim 17, wherein the chelating agent comprises ethylenediaminetetraacetic acid (EDTA).

22. The method of claim 17, wherein the boron-containing reducing agent and methoxy polyethylene glycol aldehyde have a molar ratio ranging from about 25:1 to about 5:1.

23. The method of claim 17, wherein the organic solvent comprises methylene chloride.

24. The method of claim 17, wherein the biodegradable polymer is chosen from the group consisting of a polylactide; a polyglycolide; a poly(d,1-lactide-co-glycolide); a polycaprolactone; a polyorthoester; a copolymer of a polyester and a polyether; and a copolymer of polylactide and polyethylene glycol.

25. The method of claim 17, wherein the biodegradable polymer comprises poly(d,1-lactide-co-glycolide).

26. The method of claim 1, wherein the boron-containing reducing agent and methoxy polyethylene glycol aldehyde have a molar ratio ranging from 22:1 to 5.5:1.

27. The method of claim 1, wherein the pH of the aqueous protein solution ranges from 4.0 to 4.2.

28. The method of claim 9, wherein the pH of the aqueous protein solution ranges from 4.0 to 4.2.

29. The method of claim 1, wherein the pH buffer is the acetate.

30. The method of claim 1, wherein the pH buffer is the citrate.

31. The method of claim 9, wherein the pH buffer is the acetate.

32. The method of claim 9, wherein the pH buffer is the citrate.

33. The method of claim 1, wherein the boron-containing reducing agent and methoxy polyethylene glycol aldehyde have a molar ratio ranging from 5:1 to 1.5:1.

* * * * *

UNITED STATES PATENT AND TRADEMARK OFFICE
CERTIFICATE OF CORRECTION

PATENT NO. : 10,220,075 B2
APPLICATION NO. : 15/158898
DATED : March 5, 2019
INVENTOR(S) : Mary S. Rosendahl et al.

It is certified that error appears in the above-identified patent and that said Letters Patent is hereby corrected as shown below:

In the Claims

Column 16, Line 10, Claim 20: replace "claim 18" with --claim 17--

Signed and Sealed this
Second Day of July, 2019

Andrei Iancu
*Director of the United States Patent and Trademark Office*